United States Patent
Kasprzak (10) Patent No.: US 11,471,218 B2
(45) Date of Patent: Oct. 18, 2022

(54) HAIR TRANSPLANT PLANNING SYSTEM

(71) Applicant: TrichoLAB GmbH, Bad Birnbach (DE)

(72) Inventor: Michal Kasprzak, Falenty Duze (PL)

(73) Assignee: TrichoLAB GmbH, Bad Birnbach (DE)

( * ) Notice: Subject to any disclaimer, the term of this patent is extended or adjusted under 35 U.S.C. 154(b) by 117 days.

(21) Appl. No.: 16/869,027

(22) Filed: May 7, 2020

(65) Prior Publication Data

US 2021/0059754 A1   Mar. 4, 2021

(30) Foreign Application Priority Data

Jan. 3, 2020   (EP) .................................... 20150166

(51) Int. Cl.
| | |
|---|---|
| A61B 17/50 | (2006.01) |
| G06K 9/00 | (2022.01) |
| A61B 34/10 | (2016.01) |
| A61B 34/00 | (2016.01) |
| A61B 90/25 | (2016.01) |
| A61B 90/00 | (2016.01) |
| G06T 7/00 | (2017.01) |

(52) U.S. Cl.
CPC .............. *A61B 34/10* (2016.02); *A61B 34/25* (2016.02); *A61B 90/25* (2016.02); *A61B 90/361* (2016.02);
(Continued)

(58) Field of Classification Search
USPC ....... 382/100, 103, 106, 128, 153, 168, 173, 382/181, 199, 219, 254, 276, 285–287,
(Continued)

(56) References Cited

U.S. PATENT DOCUMENTS

| 9,167,999 B2 | 10/2015 | Zhang et al. |
| 2007/0106307 A1 | 5/2007 | Bodduluri et al. |

(Continued)

FOREIGN PATENT DOCUMENTS

| EP | 3342331 A1 | 7/2018 |
| JP | 2018033897 A | 3/2018 |

OTHER PUBLICATIONS

Hillmann, et al.; Diagnosis of Hair Disorders; Seminars in Cutaneous Medicine and Surgery; Elsevier; 2009.
(Continued)

*Primary Examiner* — Seyed H Azarian
(74) *Attorney, Agent, or Firm* — Dickinson Wright PLLC; Andrew D. Dorisio (57) ABSTRACT

A system for providing images of a human scalp and associated information for assisting in hair transplant planning, the system includes a support and at least one camera selectively connectable to the support, the camera and/or the support being configured for acquiring at least one, preferably a plurality of scale calibrated overview images of the human scalp of a patient's head, preferably from different predefined angles, optical acquisition means, preferably a video-dermatoscope, being configured for acquiring a plurality of microscopic images within different regions of the scalp, a processing unit configured to process and/or analyse image data provided by the camera means and the optical acquisition means, in particular for measuring areas of the human scalp, identify and measure hair in microscopic images and/or quantitatively plan a hair transplant operation, wherein the processing unit comprises a user interface configured for interacting with a user.

15 Claims, 6 Drawing Sheets

(52) U.S. Cl.
CPC ...... *G06T 7/0012* (2013.01); *A61B 2034/107* (2016.02); *A61B 2090/3937* (2016.02); *G06T 2207/10056* (2013.01); *G06T 2207/30088* (2013.01)

(58) Field of Classification Search
USPC ............ 382/291, 312, 321; 606/133; 703/11
See application file for complete search history.

(56) References Cited

U.S. PATENT DOCUMENTS

| | | | |
|---|---|---|---|
| 2007/0150247 A1* | 6/2007 | Bodduluri | G16H 50/50 703/11 |
| 2013/0190776 A1* | 7/2013 | Zhang | A61B 17/3468 606/133 |
| 2014/0261467 A1 | 9/2014 | Zhang et al. | |
| 2016/0253799 A1* | 9/2016 | Rahman | G06T 5/002 382/128 |
| 2017/0032223 A1 | 2/2017 | Zingaretti et al. | |
| 2018/0214072 A1* | 8/2018 | Zingaretti | A61B 5/448 |
| 2018/0221094 A1* | 8/2018 | Bodduluri | G06F 3/04842 |

OTHER PUBLICATIONS

Kim, et al.; Evaluation of hair and scalp condition based on microscopy image analysis; School of Electrical Engineering; Korea University,; 2017.

Ross, et al.; Videodermoscopy in the evaluation of hair and scalp disorders; J Am Acad Dermatol; Nov. 2006.

\* cited by examiner

HAIR TRANSPLANT PLANNING SYSTEM

This application claims the benefit of German patent application no. 10 2019 123 118.3, filed Aug. 28, 2019, and European patent application no. 20 150 166.5, filed Jan. 3, 2020, the disclosures of which are incorporated herein by reference.

FIELD OF THE INVENTION

The present application relates to a hair transplant planning system. In particular, the application relates to a system for providing images and associated information of a human scalp for assisting in planning of a hair transplantation. The application also relates to a corresponding method and a computer program for these purposes.

BACKGROUND OF THE INVENTION

A hair transplant surgery requires substantial planning respectively the preparation of a personalized hair transplant plan. In general, a first step of transplant planning comprises defining the scalp regions that need to be implanted with hair, so-called "recipient regions", and regions that may be used for sourcing the hair for transplantation, so-called "donor regions". In addition, a suitable choice in terms of total amount and distribution of hair grafts to be extracted from the donor region and to be implanted in the recipient region has to be made. Hereby, hair grafts are understood as a group of one to five hairs forming a follicular unit (FU) that has to be transplanted as a whole for surviving the operation. Ideally, a suitable quantitative planning respectively a balancing of grafts to be harvested and implanted is to be carried out before the hair transplant surgery.

For providing a transplant plan, the number and quality of grafts available in the donor regions has to be taken into account, whereby the quality of grafts depends on the multiplicity of follicular units, i.e. the average number of hair shafts in an average graft, and/or the respective hair diameters. In addition, also the initial density and diameters of hair in the recipient region should be considered, in case the recipient region is not completely bald. Ideally, also a desired aesthetic effect in the recipient region and acceptable hair depletion in the donor regions has to be taken into account. The aesthetic effect is usually quantified in terms of target hair volume density or target recipient area coverage respectively cumulative hair thickness (total thickness of hair growing in 1 $cm^2$ of scalp) measuring how well the hair layer covers bald scalp once the hair grows longer. Hair volume and cumulative hair thickness depend on both, the density of hair and their thickness.

For assessing the required parameters of a patient's head before the transplant surgery, different manual procedures, algorithms and simple software programs or excel sheets are known. US 2007/0150247 A1 for example relates to a system for planning transplantation of follicular units comprising a user interface, a software-controlled processor, a monitor, and an input device, wherein the system is configured for acquiring images of the scalp, processing the images to produce a three-dimensional model of the scalp respectively the patient's head, and displaying on the three-dimensional model a proposed recipient region for implanting follicular units. During acquiring the images, the operator respectively user of the system is required to mark characteristic feature points so the captured images can be used to texture an approximate three-dimensional model of the patient's head. Although the three-dimensional model may be used to visualize recipient regions and the planned hairline to the patient before the operation, the actual determination of the above-indicated parameters is rather imprecise.

Also, a number of solutions for planning and executing robotic hair transplantation operations have been developed with focus on the detailed layout of automatically generated hair patterns, whirls and hair angulation or slanting, such as for example described in U.S. Pat. No. 9,167,999 and US 2013/190776 A1. These solutions do however not address the problem of quantitative planning of a hair transplant surgery respectively a balancing of grafts to be harvested and implanted, but rather refer to detailed problems of automated implantation.

Although the available solutions may assist a hair transplant surgeon in planning of the respective hair transplant, the results or calculations provided by the known solutions are very inaccurate and/or cumbersome. In addition, the prior art solution fail to enable a reliable assessment of the donor capacity until a shaving of a patient's head, usually carried out just before the surgery. A common problem with this procedure is that once the patient's head got trimmed for the operation, the surgeon recognizes that the dedicated donor region capacity deviates from the initially planned respectively calculated capacity and was for example overestimated due to earlier transplant operations. Hereby, unrecognized scars of the scalp or otherwise insufficient coverage may also lead to deviations from the initially prepared or calculated hair transplant plan.

The above-outlined shortcomings of the prior art transplant planning procedures and systems lead to the common problem that the scope of hair transplant operations actually performed differs substantially from what was initially planned and thus agreed on with the patient.

OBJECT AND SUMMARY OF THE INVENTION

The present invention seeks to address the above-described disadvantages and problems of the prior art. In particular, the present invention seeks to provide a system for providing an accurate yet efficient analysation of a human scalp in order to enable a more reliable determination and planning in particular of suitable donor and/or recipient regions and preferably without the need for trimming respectively clipping the patient's hair prior to analysation. In addition, the application seeks to address the provision of an optimized hair transplant plan for providing a reliable basis for a hair transplant surgery. The invention also aims at further objects and particularly the solution of other problems as will appear in the rest of the description.

In a first aspect, the invention relates to a system for providing images of a human scalp and associated information for assisting in hair transplant planning, the system comprising support means and at least one camera means selectively connectable to the support means, the camera means and/or the support means being configured for acquiring at least one, preferably a plurality of scale calibrated overview images of a human scalp of a patient's head, preferably from different predefined angles, optical acquisition means, preferably a video-dermatoscope, being configured for acquiring a plurality of microscopic images within different regions of the scalp, preferably within different regions of a respective acquired overview image, a processing unit configured to process and/or analyse image data provided by the camera means and the optical acquisition means, in particular for measuring areas of the human scalp, identify and measure hair in microscopic images and/or quantitatively plan a hair transplant operation, wherein the processing unit comprises a user interface configured for interacting with a user.

Due to the acquisition of scale calibrated overview images as well as the plurality of microscopic images of human scalp regions, the system enables an accurate and reliable assessment of the scalp and in particular of potential donor and recipient regions thereof. Hereby, the term "scale calibrated image" refers to an image taken at a predefined position and/or distance to the human scalp such as to enable a determination or calculation of reliable values for respective distances and areas from the image data. The plurality of microscopic images enables an accurate assessment of respective regions of the scalp with regards to e.g. the amount of individual hairs, amount and density of follicular units etc. and thus a quantitative planning of a hair transplant operation. The plurality of microscopic images is preferably acquired for different regions within a respective acquired overview image and in particular in different potential donor and/or recipient regions of a human scalp. The microscopic images may be acquired without the need to shave or trim respectively clip the scalp and thus, the system enables a reliable determination and planning well before the actual hair transplant surgery. Furthermore, due to the provision of camera means and optical acquisition means, the system enables a facilitated assessment and thus an efficient analysation of a human scalp, in particular without the need for manual templates or a manual analysation of photographs according to the prior art and for which no reproducible scaling can be assured.

In a preferred version, the camera means is preferably a digital photo camera and more preferably a digital SLR camera. This can be a standard digital camera known in the prior art. The digital camera preferably has a resolution of at least 6 megapixels, more preferably at least 12 megapixels. The camera means can alternatively be a digital video camera, which can provide a video signal with a frame rate of at least 25 frames per second, more preferably at least 30 frames per second. The digital video camera preferably has a resolution of at least 4K, more preferably at least 6K.

The camera means may comprise integral or external illumination means. These are preferably arranged essentially in the same direction as the camera means relative to the scalp to be captured. The illumination can be activated continuously or selectively for each frame respectively image to be captured. The illumination means are preferably designed to provide a polarized light and/or provide a light setup designed to suppress parasite reflections using for example a cross-polarization technique.

In a preferred embodiment the support means comprise a head support configured to position a patient's scalp at a fixed position with respect to the associated camera means and/or for enabling an acquisition of a plurality of overview images from the patient's scalp from predefined angles. The support means may comprise a photographic stand with dedicated support means for positioning the camera means at a fixed position with respect to the head support. Thereby, the support means are preferably configured for ensuring a reproducible geometry and fixed distance from camera to patient's head. The support means and the associated camera means may comprise as well at least two or more camera means for providing scale calibrated overview images of a patient's head.

In a preferred embodiment, the camera means and/or the support means are preferably configured for acquisition respectively capturing of different scalp regions. In particular, the camera means and/or the support means may be designed for capturing at least a vertex and frontal scalp region, a left temple scalp region, a left parieto-temporal scalp region and an occipital scalp region. The right temple and parieto-temporal scalp region may be assumed to be identical respectively symmetrical to the respective left scalp region such that the respective acquisition of images of these scalp regions may be omitted. The vertex and frontal scalp region as well as the temple scalp regions are potential recipient regions. The parieto-temporal scalp regions and an occipital scalp region are potential donor scalp regions.

The optical acquisition means is preferably a microscopic camera, preferably a video-dermatoscope. This may be provided in the form of a known special purpose digital camera combined with a high magnification polarizing lens and an illumination source such as multiple ultra-bright LEDs. The optical acquisition means is preferably designed for acquisition respectively capturing scale calibrated microscopic images of the respective scalp region. Hereby, the optical acquisition means may be positioned directly on the respective scalp region. In an alternative embodiment, the optical acquisition means may be formed by the camera means of the system, which may be selectively disconnectable from the support means in order to acquire respectively capture the microscopic images. Hereby, the camera means may comprise a dedicated microscopic imaging function.

The processing unit may comprise a personal computer with a user interface. The user interface preferably comprises at least a display and or monitor unit and a dedicated input unit such as a keyboard and/or mouse. The processing unit may at least in part be situated or provided on an external or remote server, in particular a cloud server, for carrying out at least part of the processing and/or analysing of the processing unit. The processing unit is preferably connected with the camera means and the optical acquisition means, either by means of a wired connection and/or a wireless connection.

In a preferred embodiment, the processing unit is configured for associating the microscopic images and/or data gained from the microscopic images to respective scalp regions in an acquired overview image. For this purpose, the system may comprise a dedicated positioning unit which interacts with the processing unit and/or the optical acquisition means and which is designed for providing positioning information as to where the respective microscopic images are to be captured at the scalp and thus within a respective captured overview image of the scalp. Alternatively or in addition, the processing unit may be designed for guiding a user of the system to dedicated positions of the scalp or scalp regions in which one or more microscopic images are to be captured. This may be achieved for example with dedicated visualisation on display means of the processing unit. The optical acquisition means thus enable a sampling by means of a plurality of images of the scalp in different regions. Accordingly, a precise estimation of hair statistic information for different scalp regions and for potential donor and recipient regions may be obtained. The respective hair statistic information may for example comprise at least values for an average number of hair shafts per predefined area, a number of follicular units per predefined area, an average value of hair shaft thickness per predefined area and/or a value for cumulative hair thickness density per predefined area.

In a preferred embodiment, the processing unit is configured for outputting at least one overview image of the human scalp together with a respective indication for a donor and/or recipient region and associated information based on the analysed image data, the associated information preferably comprising hair statistic information for the indicated donor and/or recipient region. The outputting respectively displaying of the at least one overview image together with a respective indication for a donor and/or recipient region as well as the associated hair statistic information provides an easy-perceivable representation of the respective scalp region and the associated parameters for that region that may support a surgeon in effective planning of a hair transplant.

In a preferred embodiment, the processing unit is configured to enable a designing and/or manually adaption of a pre-defined or proposed geometric shape and/or position of a recipient and/or donor region in an outputted overview image of the scalp. For example, the donor and/or recipient region may be indicated respectively depicted in the respective overview image as shaded or highlighted region. Thereby, borderlines may span between points respectively adorners. These may be moved respectively adjusted by a user via the user interface of the system, for example with a keyboard or a pointing device such as e.g. a mouse. This allows for adjustment of the donor/recipient region to the actual size and shape of patient's head and the hair pattern. Alternatively or in addition, the processing unit may be configured for automatically defining and/or suggesting a shape and/or position of a donor and/or recipient region based on the analysed image data.

In a preferred embodiment, the processing unit is preferably designed to suitably adjust a surface of the scalp or scalp region that is not parallel to an image plane. Hereby, the processing unit may comprise means for providing a calibration of a processing unit and/or allowing for absolute area measurement and appropriate correction for regions where the scalp surface is not coplanar with an overview image plane. For this purpose, the processing unit may comprise known algorithms for adapting respectively correcting the respective areas or measurements. In particular, the processing unit is preferably configured to correctly determine the respective areas of the scalp regions in the overview image and/or define donor and/or recipient regions based on two-dimensional images of the scalp.

In a predefined embodiment, the processing unit is configured to determine and output quantitative values for a total amount of grafts available in a defined donor region and/or a minimum value for grafts required in a defined recipient region for obtaining a predefined cumulative hair thickness value. The processing unit is preferably further configured to enable a selective adaption of a cumulative hair thickness value for obtaining a desired target recipient region coverage in a recipient region by a user. Accordingly, the system enables a quantitative planning of a hair transplant preferably for different desired target recipient region coverages of the scalp. Hereby, the system is preferably further designed to output information as to whether the analysed donor regions provide for sufficient grafts and/or to issue a warning signal in case a desired or selected target recipient region coverage cannot be obtained with the grafts available in the donor region(s).

In a further aspect the invention relates to a method of providing images of a human scalp and associated information for assisting in hair transplant planning, the method comprising the steps of acquiring at least one, preferably a plurality of scale calibrated overview images of the scalp of a patient's head, preferably from different predefined angles, by dedicated camera means, acquiring a plurality of associated microscopic images within different regions of the scalp, by optical acquisition means, preferably a video-dermatoscope, processing and/or analysing the acquired image data of the overview and microscopic images by a processing unit, outputting at least one overview image of the scalp and associated information based on the acquired image data.

In a preferred embodiment, the step of processing the image data comprises associating the microscopic images and/or data gained from the microscopic images to respective scalp regions in an acquired overview image.

In a preferred embodiment, the step of analysing the image data comprises measuring areas of the human scalp, determining the number and respective diameter values of individual hairs and/or identifying groupings of individual hairs in follicular units. The method may further comprise the step of averaging over results determined from different microscopic images from the same regions respectively donor and/or recipient regions of the scalp.

In a preferred embodiment, the method comprises the step of outputting at least one overview image of the scalp together with a respective indication for a donor and/or recipient region and associated information based on the analysed image data, the associated information preferably comprising hair statistic information for the indicated donor and/or recipient region. The hair statistic information is preferably determined based on the analysed image data and a manually adaptable graphical selection of a dedicated donor or recipient region in the image of the human scalp.

The microscopic images, in particular of potential donor regions of the human scalp are preferably acquired respectively captured without trimming respectively clipping of the hair. Preferably, the microscopic images may be captured after parting the hair at a predefined scalp region along a parting line. Thereby, the respective microscopic image is preferably captured with the parting line substantially in the middle or close to the middle of the image. The method thereby may comprise a hair parting procedure in which a plurality of parting lines are preferably manually established in the scalp region, whereby for each parting line at least one microscopic image is captured.

In a further aspect that invention relates to a computer program product comprising a computer program comprising instructions arranged to, when executed by a computer, execute at least part of the method as described above. The computer program product may be embodied on the computer readable medium such as hard disk, solid state memory, flash memory, etc., and may be non-recordable or recordable. The computer program product may comprise for example a known algorithm for image recognition and/or image measurements. These may be used for processing and analysing the image data provided by the camera means and the optical acquisition means.

In order to avoid repetitions in the present description, the skilled person is aware that the above-described features for the system- and/or method-related aspects of the invention are equally applicable to the present aspect relating to a computer program product and vice-versa. The respective features should therefore be understood as being disclosed and claimable for the present aspect relating to a computer program product and vice-versa. The same applies for the system- and method-related aspects with respect to each other.

BRIEF DESCRIPTION OF THE FIGURES

Further features, advantages and objects of the present invention will become apparent for the skilled person when taking the following detailed description of preferred embodiments into conjunction with the following figures that show.

DETAILED DESCRIPTION OF THE FIGURES

Figure 1:
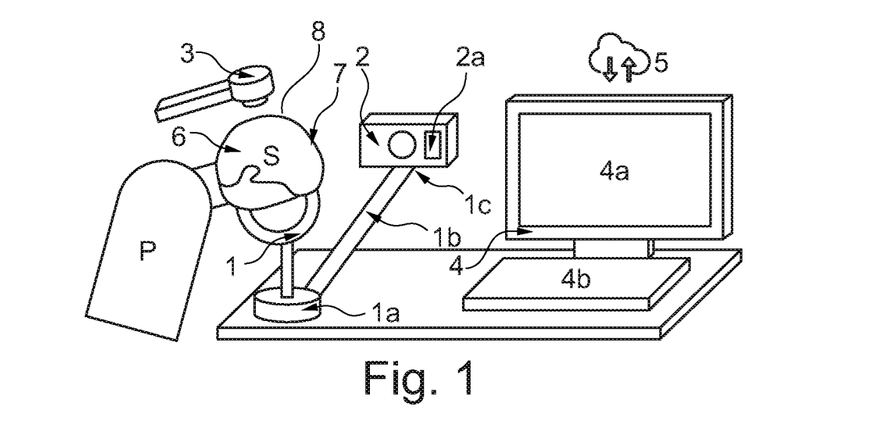
FIG. 1 a schematic side view of a preferred embodiment of a system according to the invention.

FIG. 1 relates to a preferred embodiment of a system 10 according to the invention and designed for providing images of a human scalp S and associated information for assisting in hair transplant planning. The system 10 comprises support means 1 such as a head support that is preferably configured for ensuring a reproducible position of patient's P head 8. The support means 1 preferably comprise a base 1a and a camera stand 1b, 1c connected thereto. The camera stand comprises a turnable arm 1b that is preferably designed to ensure a fixed distance between a camera means 2 connected to a support 1c of the stand and a patient's head 8 respectively a patient's scalp S of which at least one image is to be captured. The camera support 1c may be designed to selectively connect the camera means 2.

The camera means 2 preferably comprises or is preferably connected to illumination means 2a such as a polarized flash light. The camera 2 is preferably configured for capturing images of patient head 8 respectively scalp S from different and preferable predefined respectively reproducible angles and/or with preferably reproducible light setup, in particular with light setup designed to suppress parasite reflections using cross-polarization technique.

The system preferably further comprises an optical acquisition means 3, preferably a microscopic camera and more preferably a video-dermatoscope, being configured for acquiring a plurality of microscopic images within different regions of the scalp S. The optical acquisition means 3 is preferably freely movable by a user and may be used for capturing microscopic and/or contact images of the scalp S in different regions thereof, in particular in potential donor and/or recipient regions 6, 7 of the scalp S. Hereby, the microscopic images are preferably captured with prior hair parting and without trimming or clipping of the hair.

The system 10 preferably further comprises a processing unit 4, such as a computing and visualization unit. The processing unit 4 may work autonomously or may be linked via internet to an external server or image processor 5. The unit 4 is preferably designed to interact with a user via a dedicated user interface 4a, 4b comprising e.g. a display 4a and user input device such as a keyboard 4b. The display 4a and/or the input device 4b may be provided at a personal computer, a tablet or a smartphone.

The processing unit 4 is preferably linked to the camera means 2 and the optical acquisition means 3 and configured to process and/or analyse image data provided by the camera means 2 and the optical acquisition means 3, in particular for measuring areas of the human scalp S, identify and measure hair in microscopic images and/or quantitatively plan a hair transplant operation. The processing unit 4 is preferably further configured for assisting in conducting examinations and defining suitable donor and/or recipient regions 6, 7 for an analysed scalp S of the patient.

The system 10 is preferably configured for carrying out an examination respectively assessment of the scalp S of a patient P. Said examination may include at least the capturing of preferably a plurality of overview images of the patient's head 8 respectively of different scalp regions thereof using the head support 1 and sampling the different scalp regions and in particular the different potential donor and/or recipient regions by capturing a plurality of microscopic images with the optical acquisition means 3. Hereby, the processing unit 4 is preferably configured for associating the microscopic sampling images and/or data gained therefrom to respective scalp regions in an acquired overview image.

Figure 2:
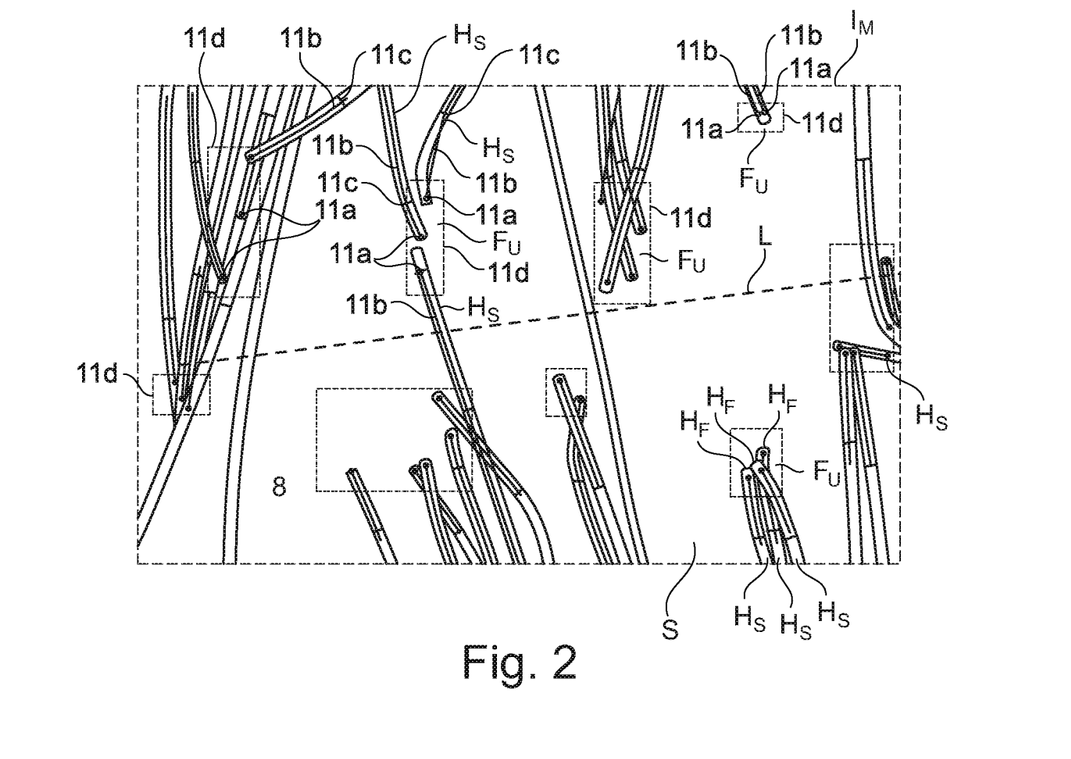
FIG. 2 a schematic example of a microscopic image of preferably non-shaved region of a human scalp captured by the system according to FIG. 1.
Figure 3A:
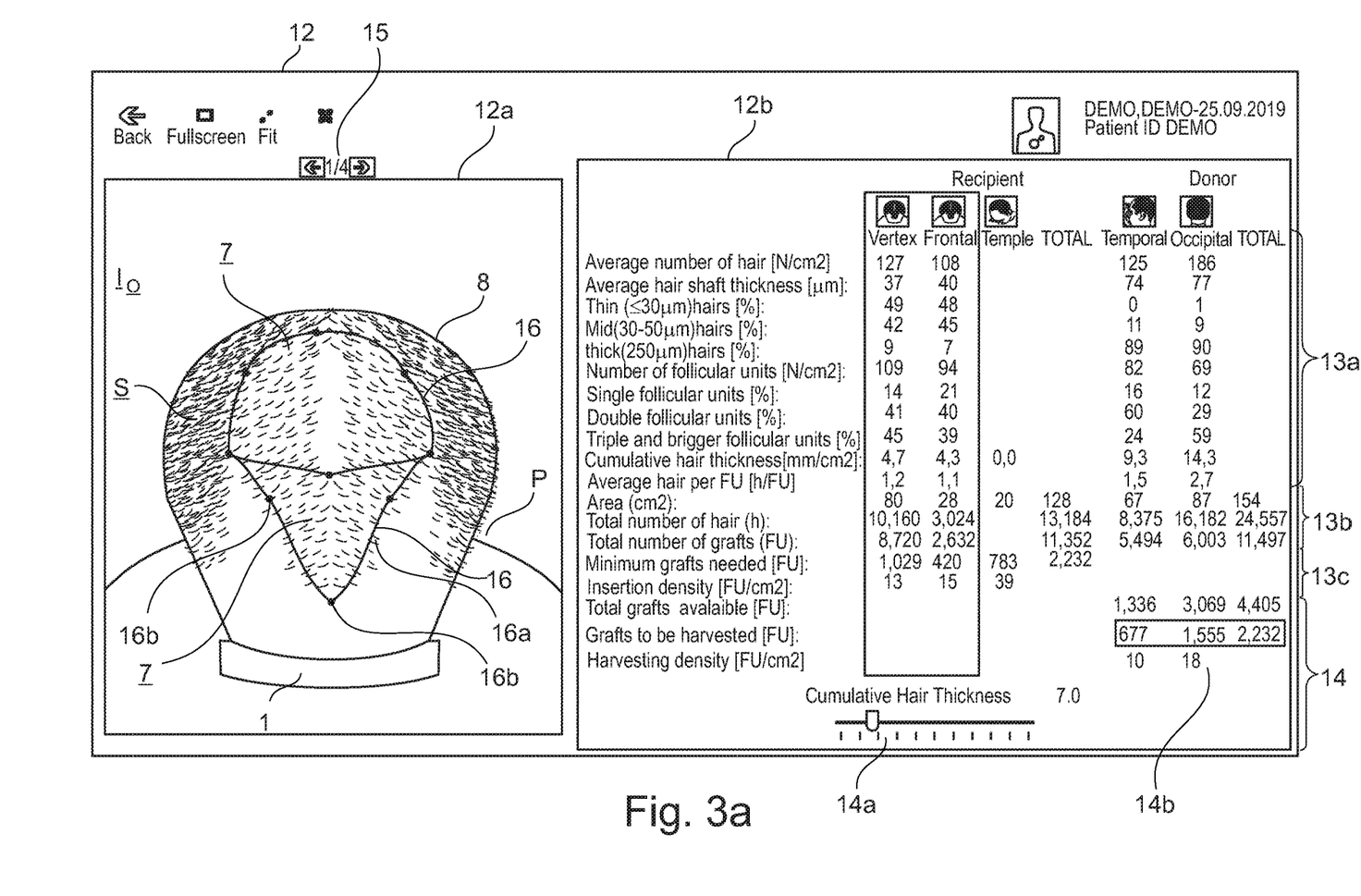
FIG. 3a,b are schematic views of a preferred visual representation of an analysed human scalp and in particular an overview image depicting a vertex and frontal scalp region as well as a temple region of the human scalp together with associated information based on captured image data respectively a visualisation of a quantitative plan for a hair transplant.
Figure 3B:
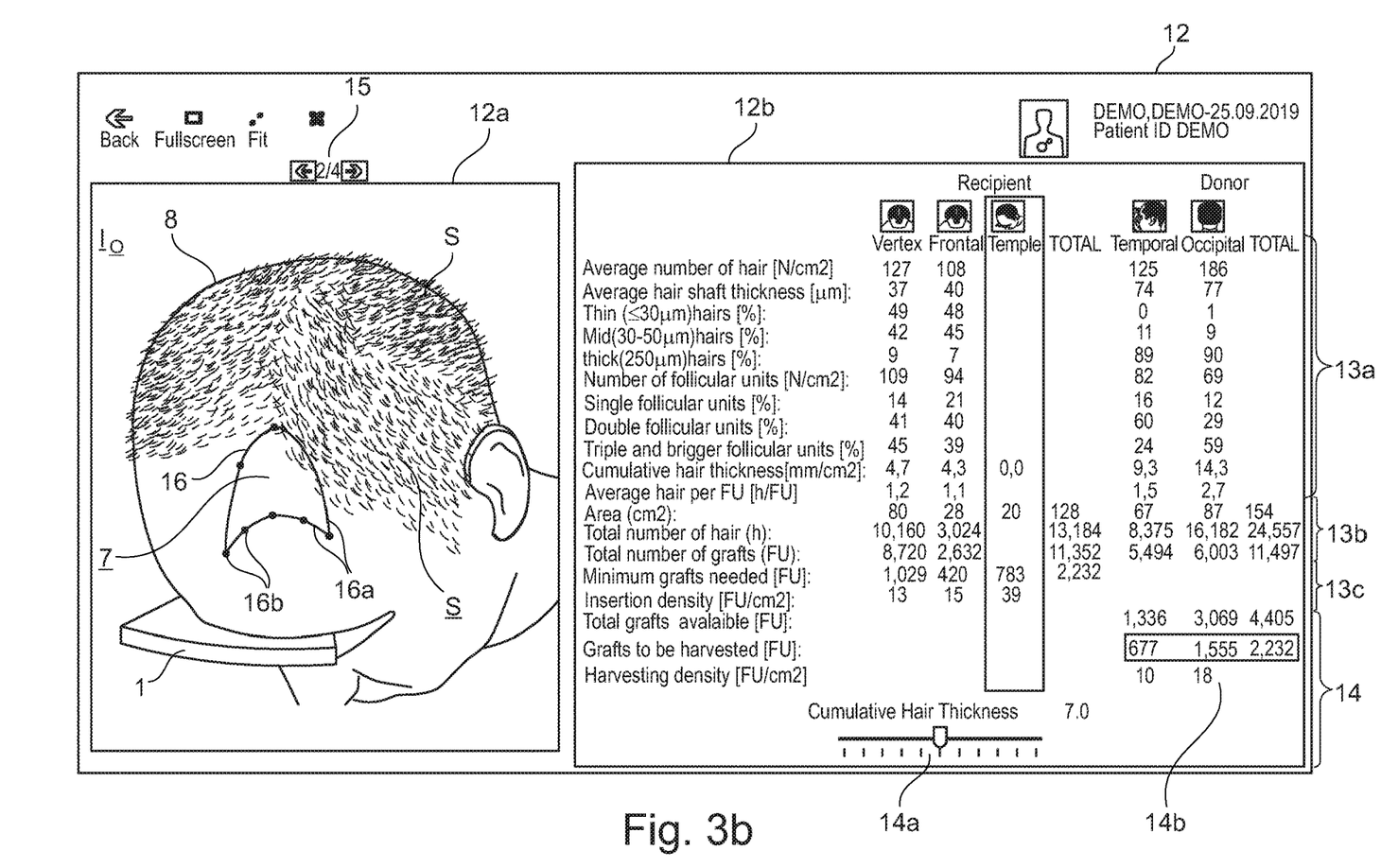

FIG. 2 relates to a schematic close-up respectively microscopic image $I_M$ of a non-shaved hair of a human scalp S that is preferably captured by the microscopic camera 3. Before the capturing of the respective image, a (manual) hair parting is preferably carried out and the image is captured with the respective parting line L preferably close to the centre of the image. This parting procedure may be provided at a plurality of different positions of the respective scalp region to be assessed with the microscopic images $I_M$. Accordingly, a plurality of sampling images $I_M$ for assessing the respective scalp regions and thus for determination of the required hair statistic information therefrom may be provided without the need of clipping or shaving the hair.

The microscopic images $I_M$ are then analysed during processing of the image data. Hereby, the processing unit 4 is preferably configured for identifying individual hair and/or grouping of individual hair into follicular units FU as well as for measuring the respective hair diameters from the provided image data.

In the shown FIG. 2, the identified hair follicles HF are marked with dots 11a and lines 11b going along each identified hair respectively along each hair shaft HS as well as with a crossing line 11c at the hair shaft HS, at which a hair diameter was measured. Further, identified follicular units FU are marked with a surrounding square 11d. This processing and/or analysation is carried out for preferably all of the captured microscopic images $I_M$ and for different regions of the analysed scalp S. Such sampling with multiple microscopic images $I_M$ enables for a precise estimation of hair statistic information for the respective scalp regions S, in particular for values for average number of hair shafts HS per predefined area, number of follicular units FU per predefined area, follicular unit density and multiplicity, average value of hair shaft thickness per predefined area, value for cumulative hair thickness density per predefined area, etc. The above indicated values for the respective parameters are preferably determined and/or calculated for each of the different regions of the analysed scalp and in particular for each of the respective potential donor and recipient regions. Hereby, an averaging over results determined from different microscopic images $I_M$ from the same potential donor or recipient region of the scalp may be carried out. By averaging over results obtained for different microscopic images from the same region the most representative values for e.g. hair density, follicular density and follicular multiplicity and average hair diameter may be derived. The microscopic image processing and/or analysation may be done automatically on the local computer or may be carried-out semi-automatically, for example with an interacting user, on a local computer or sent to remote server for processing.

FIG. 3a, 3b and FIG. 4a, 4b relate to a preferred embodiment for a visual representation of the human scalp S together with associated information for assisting in hair transplant planning, preferably carried out by a dedicated computer respectively software program and/or by the processing means 4. The shown visual representation is preferably provided by the display means 4a of the system 10 but may as well be provided by additional and/or external display respectively output means, such as in particular a tablet or smartphone that may be selectively connectable to the system 10.

The shown display or graphical visualisation 12 comprises at least an image field 12a for displaying a respective overview image $I_O$ of the scalp S of the patient P and an associated data field 12b for displaying associated information. The display 12 is further configured for displaying an indication for a respective donor and/or recipient region 6, 7. This is preferably provided in the form of a marked-up region 16 such as a shaded, surrounded or otherwise highlighted region in the respective overview image $I_O$. Thereby, borderlines 16a may span between points respectively adorners 16b for delimiting the respective region 16 for indicating the respective donor or recipient region 6, 7. The borderlines 16a and/or the points 16b may be adapted respectively moved by a user via the user interface of the system, for example with a keyboard or a pointing device such as e.g. a mouse. This allows for adjustment of the donor/recipient region 6, 7 to the actual size and shape of patient's head 8 and the hair pattern.

The data field 12b in the respective display 12 comprises hair statistic information 13a for the respective donor and/or recipient region 6, 7 based on the prior processing and/or analysation of the image data in which an area sampling with the microscopic images was carried out.

The hair statistic information 13a preferably comprises values for the average number of hair shafts per cm$^2$, the average hair shaft thickness (μm), optional a split of the hair shaft thickness distribution in three intervals, a number of follicular units per cm$^2$, and optionally a split into single hair follicular units, double hair follicular units, and multiple hair follicular units, as well as a cumulative hair thickness density, i.e. the total diameter of all the hair shafts growing in 1 cm$^2$ of scalp, which quantity best describes how well the hairs "cover" the "bald scalp".

Further, the data field 12b preferably comprises information about the area respectively an area determination 13b (in cm$^2$) of each of the recipient and donor regions 6, 7 derived from the overview images and area shapes of the regions 16 marked by the user. Hereby, a fixed geometry of the support means 1 and the associated camera means 2, a fixed distance between the camera means 2 to the patient's head, preferably in combination with geometric correction algorithm and/or proper calibration allow for very precise determination of the actual area on scalp corresponding to target/recipient shapes marked in the depicted visualisation respectively a dedicated planning program.

The data field 12b further preferably comprises overall graft information 13c respectively values for the total number of hair and grafts respectively follicular units in all of the respective donor and recipient regions.

The display 12 further comprises a planning section 14 comprising an adjustable element 14a such as a slider for setting a desired target cumulative hair thickness (7 mm/cm$^2$ in the depicted embodiment) to be obtained in the defined recipient region(s) 7. The adjustable element 14a may be operated with a keyboard, a mouse or with a touchscreen.

The planning section 14 preferably further comprises calculated values for graft transplant 14b which are dependent on the provided identified or defined recipient and donor regions 6, 7, the corresponding statistic information 13a and the set adjustable element 14a.

The calculated values for graft transplant 14b preferably comprise information respectively quantitative values for the minimum grafts that need to be implanted into each of the recipient regions (and implantation density) to reach the defined target cumulative hair thickness and/or of the total grafts theoretically available for extraction from the defined donor region(s) 6 before the cumulative hair thickness in these areas reaches the bottom limit being the target cumulative their thickness set with the adjustable element. The planning section 14 preferably further comprises information respectively quantitative values for the number of grafts that need to extract from the defined donor regions 7 (and the extraction density) to harvest enough grafts needed to achieve the desired aesthetic effect in the recipient regions.

Figure 4A:
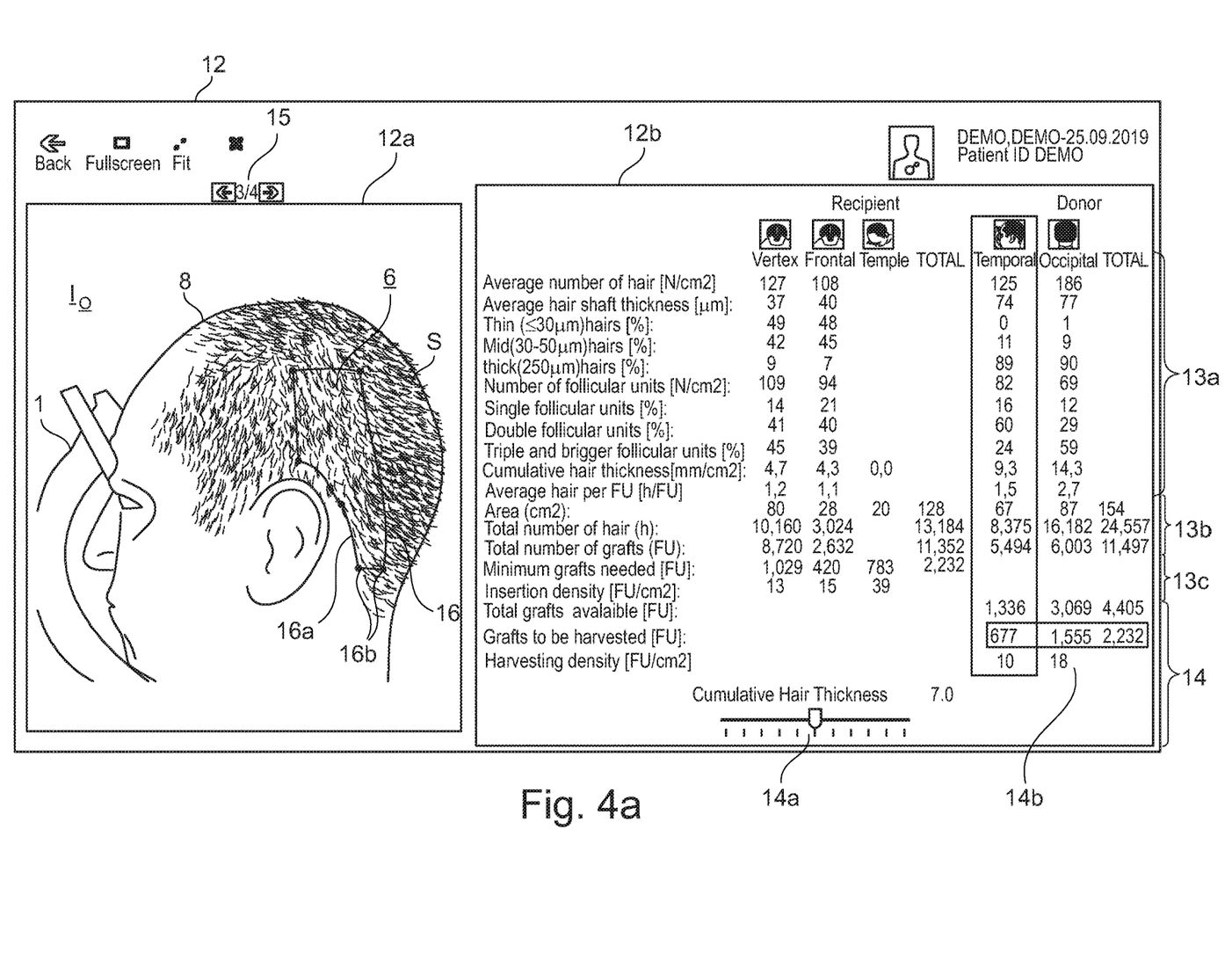
FIG. 4a, 4b are schematic views of a preferred visual representation of an analysed human scalp and in particular an overview image depicting a left parieto-temporal and occipital region of the human scalp together with associated information based on the captured image data respectively a visualisation of a quantitative plan for a hair transplant.
Figure 4B:
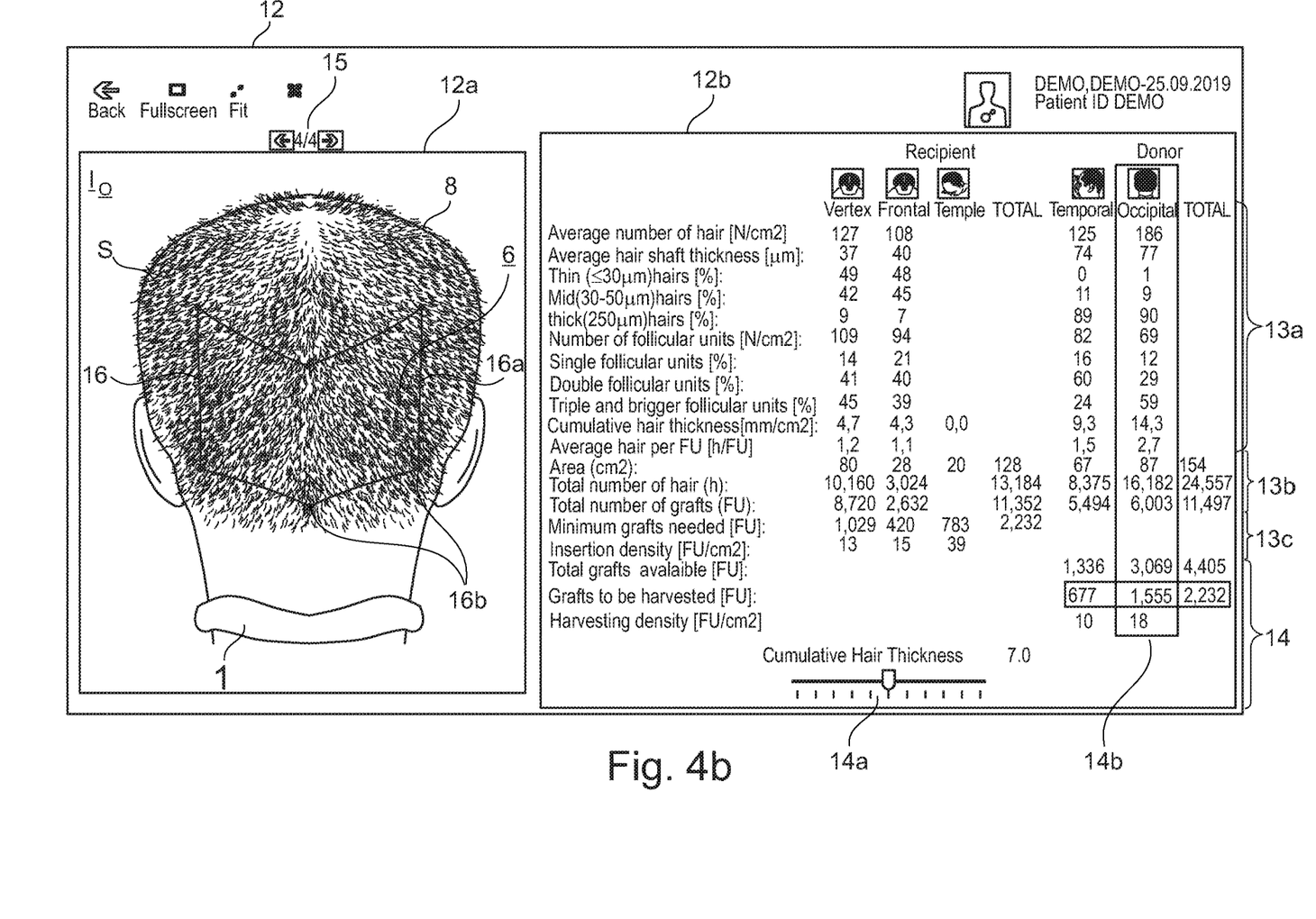

The shown embodiment in FIG. 3a, 3b, 4a, 4b relate to a transplant plan in which the user defines the planned operation areas vertex and frontal recipient regions (see FIG. 3a), left temple recipient region (see FIG. 3b), left parieto-temporal donor region (see FIG. 4a) and occipital donor region (see FIG. 4b). Hereby, the corresponding right left temple recipient region and right parieto-temporal donor region are assumed to be identical to the left regions. The respective shape of the donor and recipient regions 6, 7 may be marked-up respectively adjusted by a user in the respective overview image $I_O$. Hereby, the user may switch between different overview images and associated information as shown in these figures with respective navigation elements 15 such as arrows or tabs provided by a respective software or computer program. In this preferred planning scenario and for the indicated desired target cumulative hair thickness of 7 mm/cm$^2$, 2232 grafts need to be transplanted from the selected donor regions 6 to the selected recipient regions 7 in proportion and densities as specified in the data field 12b.

It is to be understood that the provided computer program and/or a dedicated processing unit by means of the visual representation as shown in the figures enables a facilitated and accurate evaluation of different hair transplant scenarios by selecting and/or adapting different donor and/or recipient regions as well as by selecting different target cumulative hair thickness values. Hereby, the computer program and/or the processing unit are configured for automatically calculating the number of grafts that need to be implanted into the defined recipient regions 7 and verifies if they can be safely extracted from the defined donor regions 6 without the danger of overharvesting. The user and/or a surgeon may thus simulate a plurality of possible transplant plans and/or discuss them during consultation visit with the patient prior to the operation date. Hereby, not only a desired target coverage, but also the size and shape of the respective donor and recipient regions with different positions for hairlines, temples etc may be simulated and considered.

Figure 4C:
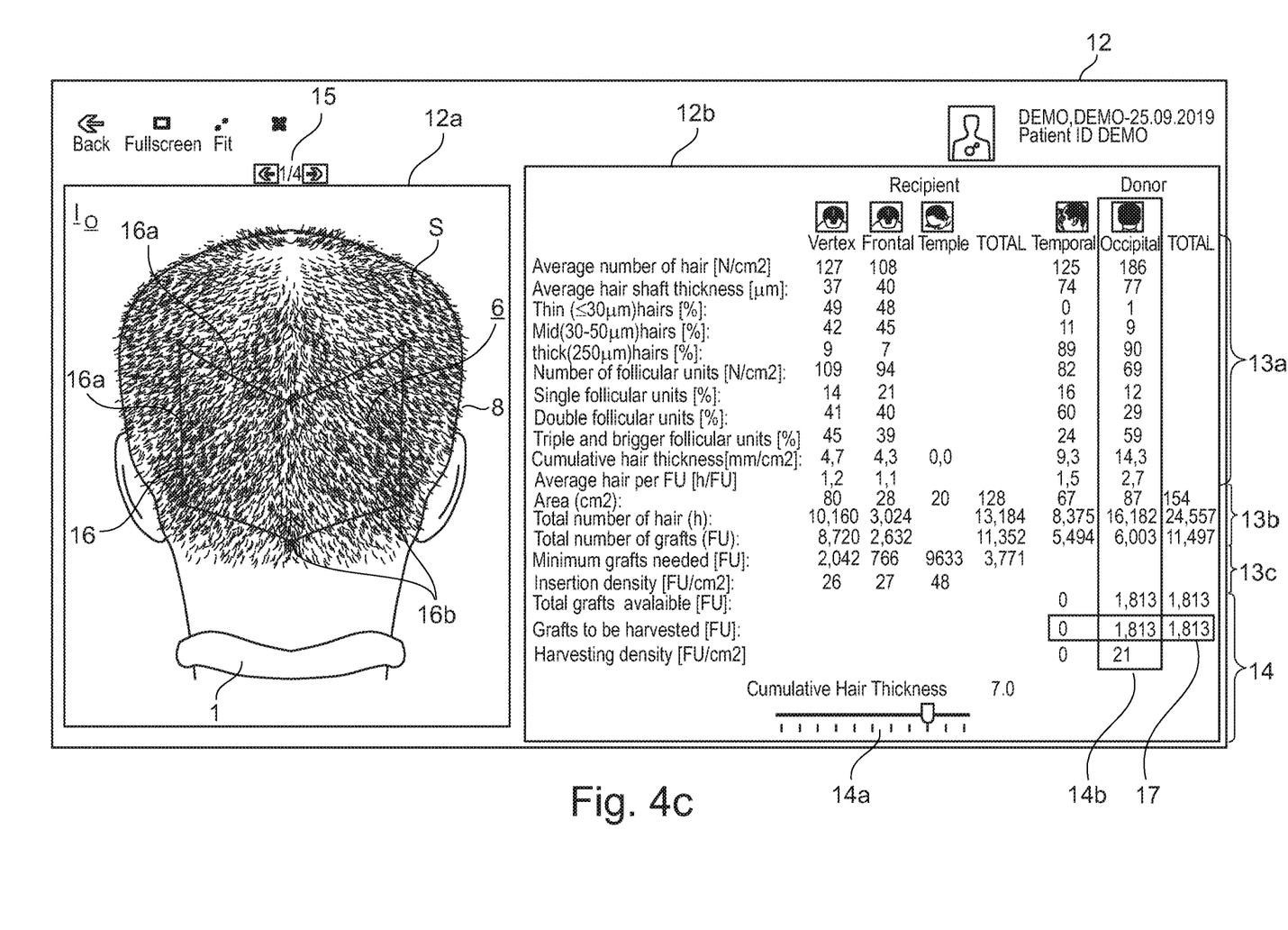
FIG. 4c is a schematic visual representation according to FIG. 4b with different associated information based on an adapted user selection concerning a desired cumulative hair thickness respectively a desired target recipient area coverage.

FIG. 4c shows an alternative hair transplant scenario for the same patient respectively based on the same evaluated hair statistic information 13a, as well as equally formed and positioned donor and recipient regions 6, 7. By contrast to the previous embodiment however, a different and in particular a substantial higher target cumulative hair thickness of 10 mm/cm² was selected by the adjustable element 14a.

In order to achieve it in all of the defined recipient regions 7 (front, vertex and temples) a relatively high number of 3771 grafts needs to implanted. Based on the provided hair statistic information, the maximum number of grafts that can be harvested from the donor regions 6 without dropping below the desired value of 10 mm/cm² in the occipital area is calculated as being 1813 which is much less than needed for the transplant. The user respectively a surgeon together with the patient may decide for this scenario as it is generally still within the donor capacity, but it is not a quantitative balanced transplant anymore and poses a danger of over-harvesting. Such scenario or choice of the user is preferably marked and/or highlighted in a predefined and preferably prominent colour scheme. In a preferred embodiment, the processing unit and/or a dedicated computer program may provide a respective alarm indicator 17, such as a visual or audio output respectively signal, for indicating such danger in the calculated scenario to a user. In the embodiment shown in FIG. 4c, a visual indication of e.g. red colour may be provided for surrounding and/or highlighting the respective quantitative values in the planning section 14.

It should be understood that the invention is not limited to the preferred embodiments as described above and various changes and modifications to the preferred embodiments will be apparent to those skilled in the art. Such changes and modifications may be made without departing from the underlying idea and scope of the present invention. Further, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the apparatus respectively system claim enumerating several means, several of these means may be embodied by one and the same item of hardware. The mere fact that certain measures are recited in mutually different dependent claims does not indicate that a combination of these measures cannot be used to advantage.

LIST OF REFERENCE NUMERALS 1 support means
1a support means base
1b camera stand
1c camera support
1c camera means
2a illumination means
3 optical acquisition means/video-dermatoscope
4 processing unit
4a, 4b user interface
5 cloud, external server or image processor
6 donor region
7 recipient region
8 head
10 transplant planning system
11a marker for hair follicles
11b marker for course of individual hair
11c marker for hair diameter measurement
11d marker for identified follicular unit
12 display
12a image field
12b data field
13a hair statistic information
13b area determination
13c overall graft information
planning section
14a adjustable element
14b calculated values for graft transplant
15 navigation elements
16 marked-up region
16a borderlines
16b points
17 alarm indicator
FU follicular unit
HF hair follicle
HS hair shaft
$I_M$ exemplary schematic microscopic image
$I_O$ exemplary schematic overview image(s)
P patient
S scalp

The invention claimed is:

1. A system (10) for providing images of a human scalp (S) and associated information for assisting in hair transplant planning, the system comprising:
    a support (1) and at least one camera (2) selectively connectable to the support, the at least one camera (2) being configured for acquiring at least one scale calibrated overview image of a human scalp (S) of a patient's head (8),
    a microscopic camera, being configured for acquiring a plurality of microscopic images within different regions of the scalp (S),
    a processing unit (4) configured to process or analyze image data provided by the camera (2) and the microscopic camera (3), for measuring areas of the human scalp (S), identify and measure hair in microscopic images or quantitatively plan a hair transplant operation,
    wherein the processing unit (4) comprises a user interface (4a,4b) configured for interacting with a user; and
    wherein the support (1) comprises a head support configured to position a patient's scalp (S) at a fixed position with respect to the associated camera (2) and for enabling an acquisition of a plurality of overview images from the patient's scalp (S) from predefined angles.

2. The system according to claim 1, wherein the processing unit (4) is configured for associating the microscopic images or data gained from the microscopic images to respective scalp regions in the acquired scale calibrated overview image.

3. The system according to claim 1, wherein the processing unit (4) is configured for outputting at least one overview image of the human scalp (S) together with a respective indication for a donor region, a recipient region, or a donor and recipient region (6,7), and associated information based on the analyzed image data, the associated information comprising hair statistic information for the indicated donor or recipient region (6,7).

4. The system according to claim 3, wherein the hair statistic information comprises at least values for an average number of hair shafts per predefined area, a number of follicular units per predefined area, an average value of hair shaft thickness per predefined area or a value for cumulative hair thickness density per predefined area.

5. The system according to claim 1, wherein the processing unit (4) is configured to enable a designing or manually adaption of a pre-defined or proposed geometric shape of a recipient or donor region, position of a recipient or donor region (6,7), or a geometric shape and position of a recipient or donor region, in an outputted overview image of the scalp (S).

6. The system according to claim 5, wherein the processing unit (4) is configured to determine and output quantitative values for a total amount of grafts available in a defined donor region (6) or a minimum value for grafts required in a defined recipient region (7) for obtaining a predefined cumulative hair thickness value.

7. The system according to claim 6, wherein the processing unit (4) is configured to enable a selective adaption of a cumulative hair thickness value for obtaining a desired target recipient region coverage in a recipient region (7) by a user.

8. The system of claim 1, wherein the microscopic camera comprises a video-dermatoscope.

9. A method of providing images of a human scalp (S) and associated information for assisting in hair transplant planning, the method comprising the steps of:
- acquiring at least one, scale calibrated overview image of the scalp (S) of a patient's head (8), by a camera (2) associated with a support (1), wherein the support (1) comprises a head support configured to position the patient's scalp (S) at a fixed position with respect to the camera (2) and for enabling an acquisition of the at least one scale calibrated overview image of the patient's scalp (S) from predefined angles,
- acquiring a plurality of associated microscopic images within different regions of the scalp (S), by a microscopic camera,
- processing or analyzing the acquired image data of the at least one scale calibrated overview image and microscopic images by a processing unit (4),
- said processing or analyzing step comprising measuring areas of the human scalp (S), identifying and measuring hair in microscopic images, and quantitatively planning a hair transplant operation,
- outputting at least one overview image of the scalp (S) and associated information based on the acquired image data.

10. The method according to claim 9, wherein the step of processing the image data comprises associating the microscopic images or data gained from the microscopic images to respective scalp regions in an acquired overview image.

11. The method according to claim 9, wherein the step of analyzing the image data comprises measuring areas of the human scalp (S), determining the number and respective diameter values of individual hairs or identifying groupings of individual hairs in follicular units.

12. The method according to claim 9, wherein the method comprises the step of outputting at least one overview image of the human scalp (S) together with a respective indication for a donor or recipient region (6,7) and associated information based on the analyzed image data, the associated information preferably comprising hair statistic information for the indicated donor or recipient region (6,7).

13. The method according to claim 12, wherein the hair statistic information is determined based on the analyzed image data and a manually adaptable graphical selection of a dedicated donor or recipient region (6,7) in the image of the human scalp (S).

14. The method according to claim 9, wherein the microscopic images, of potential donor regions (6) of the scalp (S) are acquired during a hair parting procedure.

15. A computer program product comprising a computer program comprising non-transitory computer readable medium instructions arranged to, when executed by a computer, execute at least part of the method according to claim 9.

* * * * *